United States Patent
Frazier

(10) Patent No.: US 8,697,004 B2
(45) Date of Patent: Apr. 15, 2014

(54) SEQUENCING SYSTEM WITH MEMORY

(75) Inventor: Jeffery D. Frazier, Portola Valley, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 381 days.

(21) Appl. No.: 12/783,262

(22) Filed: May 19, 2010

(65) Prior Publication Data

US 2010/0262379 A1  Oct. 14, 2010

Related U.S. Application Data

(60) Continuation of application No. 12/156,583, filed on Jun. 3, 2008, now abandoned, which is a continuation-in-part of application No. 10/455,986, filed on Jun. 7, 2003, now Pat. No. 7,381,315, which is a division of application No. 09/938,767, filed on Aug. 24, 2001, now Pat. No. 6,627,433, said application No. 12/783,262 is a continuation-in-part of application No. 10/800,388, filed on Mar. 12, 2004, now abandoned, which is a division of application No. 09/955,608, filed on Sep. 19, 2001, now Pat. No. 6,726,820.

(51) Int. Cl.
*G01N 33/48* (2006.01)

(52) U.S. Cl.
USPC .......... 422/400; 422/68.1; 422/417; 204/450; 204/451; 204/456; 210/198.2; 210/656; 356/344

(58) Field of Classification Search
USPC ................. 422/68.1, 417; 204/450, 451, 456; 210/198.2, 656; 356/344
See application file for complete search history.

(56) References Cited

U.S. PATENT DOCUMENTS

| | | | |
|---|---|---|---|
| 4,832,815 A | 5/1989 | Kambara et al. |
| 4,908,112 A | 3/1990 | Pace |
| 5,062,942 A | 11/1991 | Kambara et al. |
| 5,114,551 A | 5/1992 | Hjerten et al. |
| 5,190,632 A | 3/1993 | Fujimiya et al. |
| 5,192,412 A | 3/1993 | Kambara et al. |
| 5,252,294 A | 10/1993 | Kroy et al. |
| 5,268,080 A | 12/1993 | Kambara et al. |
| 5,277,780 A | 1/1994 | Kambara |
| 5,307,148 A | 4/1994 | Kambara et al. |
| 5,314,602 A | 5/1994 | Kambara et al. |

(Continued)

FOREIGN PATENT DOCUMENTS

| | | |
|---|---|---|
| EP | 0 376 611 | 7/1990 |
| EP | 0 840 115 | 6/1998 |

(Continued)

OTHER PUBLICATIONS

Huang et al., Acousto-Optical Deflection-based Laser Beam Scanning for Fluorescence Detection on Mulitchannel Electrophoretic Microchips, *Anal. Chem.*, vol. 71, No. 23, pp. 5309-5314 (1999).

(Continued)

*Primary Examiner* — Lyle Alexander

(57) ABSTRACT

The present teachings provide a device including a memory. According to various embodiments, the memory is readable, writable, and rewritable. The present teachings further provide processing stations, e.g., for carrying out electrophoresis, per, genetic analysis, sample preparation, and/or sample cleanup, etc., that are capable of reading from and/or writing/rewriting to such memory.

12 Claims, 9 Drawing Sheets

(56) References Cited

U.S. PATENT DOCUMENTS

| | | | |
|---|---|---|---|
| 5,384,028 A | 1/1995 | Ito | |
| 5,439,578 A | 8/1995 | Dovichi et al. | |
| 5,529,679 A | 6/1996 | Takahashi et al. | |
| 5,552,028 A | 9/1996 | Madabhushi et al. | |
| 5,582,705 A | 12/1996 | Yeung et al. | |
| 5,585,069 A | 12/1996 | Zanzucchi et al. | |
| 5,641,400 A | 6/1997 | Kaltenbach et al. | |
| 5,641,634 A | 6/1997 | Mandecki | |
| 5,695,626 A | 12/1997 | Yeung et al. | |
| 5,741,411 A | 4/1998 | Yeung et al. | |
| 5,741,462 A | 4/1998 | Nova et al. | |
| 5,751,629 A | 5/1998 | Nova et al. | |
| 5,770,455 A | 6/1998 | Cargill et al. | |
| 5,790,727 A | 8/1998 | Dhadwal et al. | |
| 5,833,827 A | 11/1998 | Anazawa et al. | |
| 5,867,266 A | 2/1999 | Craighead | |
| 5,874,214 A | 2/1999 | Nova et al. | |
| 5,925,562 A | 7/1999 | Nova et al. | |
| 6,013,168 A | 1/2000 | Arai | |
| 6,017,434 A * | 1/2000 | Simpson et al. | 204/612 |
| 6,025,129 A | 2/2000 | Nova et al. | |
| 6,090,251 A | 7/2000 | Sundberg et al. | |
| 6,094,137 A | 7/2000 | Rasch et al. | |
| 6,103,199 A | 8/2000 | Bjornson et al. | |
| 6,132,685 A | 10/2000 | Kercso et al. | |
| 6,149,058 A * | 11/2000 | Albaret | 235/380 |
| 6,159,353 A | 12/2000 | West et al. | |
| 6,201,474 B1 | 3/2001 | Brady et al. | |
| 6,206,292 B1 | 3/2001 | Robertz et al. | |
| 6,211,781 B1 | 4/2001 | McDonald | |
| 6,236,945 B1 | 5/2001 | Simpson et al. | |
| 6,246,046 B1 | 6/2001 | Landers et al. | |
| 6,258,606 B1 | 7/2001 | Kovacs | |
| 6,300,141 B1 | 10/2001 | Segal et al. | |
| 6,317,028 B1 | 11/2001 | Valiulis | |
| 6,319,668 B1 | 11/2001 | Nova et al. | |
| 6,329,139 B1 | 12/2001 | Nova et al. | |
| 6,352,854 B1 | 3/2002 | Nova et al. | |
| 6,359,444 B1 | 3/2002 | Grimes | |
| 6,361,950 B1 | 3/2002 | Mandecki | |
| 6,372,428 B1 | 4/2002 | Nova et al. | |
| 6,376,187 B1 | 4/2002 | Mandecki | |
| 6,387,623 B1 | 5/2002 | Mandecki | |
| 6,406,848 B1 | 6/2002 | Bridgham et al. | |
| 6,417,010 B1 | 7/2002 | Cargill et al. | |
| 6,454,924 B2 | 9/2002 | Jedrzejewski et al. | |
| 6,458,259 B1 | 10/2002 | Parce et al. | |
| 6,483,434 B1 | 11/2002 | UmiKer | |
| 6,520,544 B1 | 2/2003 | Mitchell et al. | |
| 6,541,211 B1 | 4/2003 | Patek et al. | |
| 6,654,505 B2 | 11/2003 | Bridgham et al. | |
| 6,806,052 B2 | 10/2004 | Bridgham et al. | |
| 6,831,994 B2 | 12/2004 | Bridgham et al. | |
| 6,969,488 B2 | 11/2005 | Bridgham et al. | |
| 7,061,379 B2 | 6/2006 | Chen et al. | |
| 7,091,864 B2 | 8/2006 | Veitch et al. | |
| 7,282,370 B2 | 10/2007 | Bridgham et al. | |
| 2001/0021356 A1 | 9/2001 | Konrad | |
| 2002/0018733 A1 | 2/2002 | Kapplein et al. | |
| 2002/0030598 A1 | 3/2002 | Dombrowski et al. | |
| 2002/0076819 A1 | 6/2002 | Bowman et al. | |
| 2002/0094515 A1 | 7/2002 | Erlach et al. | |
| 2002/0098472 A1 | 7/2002 | Erlach et al. | |
| 2002/0098598 A1 | 7/2002 | Coffen et al. | |
| 2002/0111551 A1 | 8/2002 | Erlach et al. | |
| 2002/0114739 A1 | 8/2002 | Weigl et al. | |
| 2003/0017082 A1 | 1/2003 | van Deursen et al. | |
| 2003/0072676 A1 | 4/2003 | Fletcher-Haynes et al. | |
| 2003/0087455 A1 | 5/2003 | Eggers et al. | |
| 2003/0124539 A1 | 7/2003 | Warrington et al. | |
| 2003/0211012 A1 | 11/2003 | Bergstrom et al. | |
| 2004/0029109 A1 | 2/2004 | Lai | |
| 2004/0100415 A1 | 5/2004 | Veitch et al. | |
| 2004/0121432 A1 | 6/2004 | Klein et al. | |
| 2004/0131505 A1 | 7/2004 | Koeda | |
| 2004/0173508 A1 | 9/2004 | Deursen et al. | |

FOREIGN PATENT DOCUMENTS

| | | |
|---|---|---|
| JP | 57-070459 | 4/1982 |
| JP | 05-079469 | 10/1993 |
| JP | 09-049793 | 2/1997 |
| JP | 2000-507695 | 6/2000 |
| JP | 2000-258392 | 9/2000 |
| JP | 2001-188601 A | 7/2001 |
| JP | 2004-93519 A | 3/2004 |
| WO | WO 96/08433 | 3/1996 |
| WO | WO 01/47638 A2 | 7/2001 |

OTHER PUBLICATIONS

Wang et al., Microfabricated Electrophoresis Chips for Simultaneous Bioassays of Glucose, Uric Acid, Ascorbic Acid, and Acetaminophen, *Anal. Chem.*, vol. 72, No. 11, pp. 2514-2518 (2000).

Cheng et al., Development of a Multichannel Microftuidic Analysis System Employing Affinity Capillary Electrohoresis for Immunoassay, *Anal. Chem.*, vol. 73. No. 7. pp. 1472-1479 (2001).

Tian et al., Capillary and Microchip Electrophoresis for Rapid Detection of Known Mutations by Combining Alle-Specific DNA Amplification with Heteroduplex Analysis, *Clinical Chem.*, vol. 42, No. 2, pp. 73-185.

Birge, R. R., Protein-Based Three-Dimensional Memory—A light absorbing molecule from bacteria could provide faster access time and denser data storage in three-dimensional optical memories, *American Scientist*, vol. 82, pp. 346-355 (1994).

Birge, R. R., et al., Biomolecular Electronics: Protein-Based Associative Processors and Volumetric Memories, *J. Phys. Chem. B*, vol. 103, pp. 10746-10766 (1999).

Henke, Cliff, DNA-chip technologies—Part 1: Research fundamentals and industry catalysts, *IVD Technology Magazine*, (Sep. 1998).

Henke, Cliff, DNA-Chip technologies—Part 2: State-of-the-art and competing technologies, *IVD Technology Magazine*, (Nov. 1998).

Henke, Cliff, DNA-chip technologies—Part 3: What dos the future hold?, *IVD Technology Magazine*, (1998).

Frost, Pam, Tiny Channels Carved in Plastic Enable Medical Test on a CD. *Ohio State Research News*, (2000).

New RFID Tag with More Memory, RFID Journal, Aug. 25, 2003.

Inventor's Relationship, Vincogen web page downloaded for http://www.vincogen.com/technology.htm on Jan. 29, 2004.

Technology, Vincogen web page downloaded from http://www.vincogen.com/technology.htm on Jan. 29, 2004.

Illustration of a Microtransponder for DNA-Probe Assays, Pharmaseq web page downloaded from http://www.pharmaseq.com/illustration.html on Sep. 23, 2004.

* cited by examiner

SEQUENCING SYSTEM WITH MEMORY

CROSS REFERENCE TO RELATED APPLICATIONS

This application is a continuation of U.S. patent application Ser. No. 12/156,583, filed Jun. 3, 2008 (now abandoned), which is a continuation-in-part of U.S. patent application Ser. No. 10/455,986, filed Jun. 7, 2003 (now U.S. Pat. No. 7,381,315), which is a divisional of U.S. patent application Ser. No. 09/938,767, filed Aug. 24, 2001 (now U.S. Pat. No. 6,627,433), and U.S. patent application Ser. No. 12/156,583 is a continuation-in-part of U.S. patent application Ser. No. 10/800,388, filed Mar. 12, 2004 (now abandoned), all of which are incorporated herein in their entireties by reference.

FIELD OF THE INVENTION

The present teachings relate to microdevices, such as those used in the pharmaceutical and biotechnological fields, and to analyte-separation devices. The present teachings also relate to electrophoretic separation systems for the analysis of biomolecules, such as nucleic acids.

BACKGROUND OF THE INVENTION

In low-throughput situations, sample tracking and record keeping can often be handled adequately in a manual fashion. For example, one or several words about a sample, and/or an alphanumeric identifier, can be written or typed on a label that is applied to a container holding the sample. In some cases, additional (e.g., more detailed) information is kept in paper form, e.g., notebooks, and/or manually entered into a spreadsheet or database on a computing device, such as a personal computer (PC).

With the advent of medium- to high-throughput sample processing, it has become more challenging to track each sample and maintain information on it for ready accessing. Providing sample containers with bar codes has provided some advantages in sample tracking. As a practical matter, a bar code, per se, carries very little information, simply being an identifier. Further, there is a lower limit on the size of container with which a bar code can be used. In addition, a bar code itself is static information. That is, once a bar code is written and placed on a sample container, it cannot be readily changed.

Sample tracking and information maintenance in sequencing operations will become even more challenging as the industry moves toward microdevice, very high-throughput formats.

In an effort to meet the challenges presented by very high-throughput sample processing, a great deal of effort has been focused on software and networking solutions to large-scale information management. It is envisioned that software and networking technologies will permit instruments and applications of all types to communicate with one another and to share database resources for tracking the many, many samples being processed. Many of today's popular commercial LIMS (laboratory information management systems), for example, are moving toward the use of open systems architectures and platforms to offer client/server capabilities and enterprise-wide access to lab information.

Notwithstanding the advantages offered by such LIMS, it will happen that a sample, or many samples in a microdevice, will need to be physically transported between sites, machines and/or computers that are not connected by a network or LIMS.

The present teachings also relate to devices for carrying out separations of analytes, such as biomolecules (e.g., proteins, DNA, RNA, etc.), which have gained widespread use in recent years. In electrophoretic separations, it is often desirable to illuminate a plurality of migrating analytes, tagged with excitable reporters (e.g., fluorescent dyes), to stimulate detectable emission indicative of the nature (e.g., identity or composition) of the tagged analytes.

SUMMARY OF THE INVENTION

Aspects of the invention provide a device including a memory integrated into the device. The memory can be, for example, a readable-writable-rewritable memory (also referred to herein simply as a "rewritable" memory).

Further aspects of the invention provide a sample-processing station (e.g., for genetic analysis, electrophoresis, per, sample preparation and/or sample cleanup, etc.) configured for reading from, and/or writing/rewriting to, the memory integrated into a device.

A wide variety of information can be written to the memory of a device. For example, sample ID, sample history, sample lineage, a person's notes pertaining to a sample, nucleic acid sequence information, and the like. In various embodiments, a memory that is integrated into a substrate defining, at least in part, a device carries instructions that can be read by an apparatus for acting on samples held by the device, which the apparatus can read and carry out. Optionally, the apparatus can then write to the memory of the device (e.g., results pertaining to the act(s) performed, etc.).

A microdevice of the invention can be transported from one place to another, and the memory accessed at each location. The information (written to the integrated memory) and the microdevice (including any sample(s) therein) can conveniently be transported and/or stored (etc.) as a unit.

A microdevice of the present invention can find use alone, or in combination with one or more other sample tracking and information storage/retrieval technologies, such as those previously discussed.

Among other things, the present invention provides advancements in methods and devices for tracking samples, and/or storing and retrieving information pertaining thereto. Such advancements can be used as an alternative or a supplement to known methods and devices, such as those previously discussed.

Aspects of the invention provide a microdevice, various embodiments of which comprise a substrate or body, such as a plate, wafer, chip, slide, disc, or the like, including one or more microfluidic structures (e.g., channels, wells, chambers, reservoirs, or any combination thereof), and a readable-writable-rewritable memory integrated into the substrate, with the memory being adapted for storing binary coded information.

In various embodiments, at least one of the one or more microfluidic structures comprises a channel having a cross-sectional dimension of no greater than 500 micrometers (e.g., no greater than 250 micrometers, no greater than 100 micrometers, or no greater than 75 micrometers).

According to various embodiments, one or more of the microfluidic structures comprises a chamber, well or reservoir configured to hold a micro-volume of a fluidic sample, the micro-volume being no more than about 250 µl (e.g., about 100 µl, 75 µl, 50 µl, or less).

According to various embodiments, the integrated memory can be permanently fixed in or to the substrate, or it can be removably attached to the substrate.

In various embodiments, the memory is selected from the group consisting of integrated circuit memories, optical memories, thin film semi-conductor memories, ferromagnetic memories, molecular memories, biomolecular memories, and any combination thereof.

Various embodiments further include a microcontroller chip supported by (e.g., integrated into) the substrate and adapted for communication with the memory.

In various embodiments, machine-readable computer code is stored in the memory.

According to various embodiments, at least one read-only memory is also integrated into the substrate.

Further aspects of the invention provide an electrophoresis microdevice, various embodiments of which comprise a substrate including one or more microscale structures configured to support one or more fluidic samples; and a readable-writable-rewritable memory integrated into the substrate.

According to various embodiments, an electrophoresis microdevice can further include (i) one or more electrodes (e.g., microelectrodes integrated into the substrate), and (ii) a power source (e.g., a DC power source); with the one or more electrodes being connectable to the power source to generate one or more electrical fields along at least one of the one or more microscale structures.

In another of its aspects, the present invention provides a thermal cycling microdevice, various embodiments of which include a substrate including one or more microscale structures (e.g., wells or reservoirs) adapted to receive or support one or more biomolecule-containing samples (e.g., DNA-containing samples); a readable-writable-rewritable memory integrated into a region of the substrate; and a temperature control element or device, adapted to modulate (cycle) the temperature within at least one of the one or more microscale structures.

Another aspect of the present invention provides an apparatus for acting on one or more biomolecule-containing samples supported by a microdevice, such as a microdevice including an integrated readable-writable-rewritable memory. In various embodiments, an apparatus includes: a housing; a reader-writer unit mounted in the housing, with the reader-writer unit being adapted to receive a region of the microdevice into which the memory is integrated; and a support mounted in the housing, for holding the microdevice while the samples are acted upon and while the memory region is received within the reader-writer unit.

According to various embodiments, an apparatus further includes a detector operably coupled to a region whereat a microdevice is located when held by the support.

In various embodiments, an apparatus further comprises a temperature control module adapted to regulate the temperature of at least a portion of a microdevice when held by the support.

According to various embodiments, an excitation-beam source (e.g., a laser) is configured to direct an excitation beam of light along an optical path leading to a region whereat a microdevice is located when held by the support.

Further aspects of the present invention provide a system for acting on samples, and storing and retrieving information pertaining thereto. According to various embodiments, the system comprises: a microdevice including one or more microfluidic structures adapted to support at least one biomolecule-containing sample; a readable-writable-rewritable memory integrated into the microdevice; and a reader-writer unit adapted to receive the memory and to read from, and write/rewrite to, the memory.

In various embodiments, a system further includes a sample-processing station; with the reader-writer unit being mounted in the station.

According to various embodiments, the memory of a system has a storage capacity of at least 500 kilobytes (e.g., at least 1 megabyte, at least 10 megabytes, at least 100 megabytes, or greater).

In another of its aspects, the present invention provides a method for acting on one or more fluidic samples, and storing and retrieving information pertaining thereto. In various embodiments, a method comprises: (i) providing a microdevice comprising a substrate including one or more microfluidic structures, and a readable-writable-rewritable memory integrated into the substrate; (ii) manipulating one or more fluidic samples in the microfluidic structures; and (iii) storing binary coded information in the memory pertaining to the one or more samples.

In various embodiments, the one or more microfluidic structures are selected from the group consisting of channels, chambers, wells, reservoirs, and any combination thereof.

According to various embodiments, the manipulating step comprises electrophoresing at least one of the one or more fluidic samples.

In various embodiments, the one or more fluidic samples includes one or more polynucleotides. Additionally, the manipulating step can comprise amplifying at least one of the one or more polynucleotides (e.g., by polymerase chain reaction (per)).

According to various embodiments, at least 500 kilobytes (e.g., at least 750 kilobytes, at least 1 megabyte, at least 10 megabytes, or more) of information is stored in the memory.

Further aspects of the present invention provide a microdevice, various embodiments of which comprise a substrate including means for supporting one or more biomolecule-containing samples; and means for storing binary coded information integrated into the substrate.

In various embodiments, the means for storing includes a storage capacity of at least 500 kilobytes (e.g., at least 750 kilobytes, at least 1 megabyte, at least 10 megabytes, or more).

According to various embodiments, the means for storing comprises a readable-writable-rewritable memory structure.

Various aspects of the present invention provide a multi-channel analyte-separation device (channel device) comprising a substrate defining an array of channels. According to various embodiments, adjacent channels of the device are separated by wall structure, which includes at least a portion that is substantially transparent. The transparent portions are disposed along a path or line crossing (e.g., co-planar and normal to) the longitudinal axes of the channels. An excitation-beam source (e.g., a laser) is adapted to direct an excitation beam of light along the path, such that the beam can simultaneously pass through each of the transparent portions and each of the channels. Plural samples migrating along the various channels, e.g., by electrophoresis, can thus be simultaneously irradiated and detected.

Various embodiments are particularly adapted to bio-molecule (e.g., DNA, RNA, PNA, etc.) sequence or other analysis methods, in which each of a plurality of different fragment types is labeled with a spectrally distinctive fluorescent dye. According to certain embodiments, a side-entry laser arrangement at a detection zone of a multi-channel electrophoresis device excites the dyes, while in the channels, to emit light. In various embodiments, emitted light from samples in the channels passes through a laser light filter, through a collection lens, through a transmission dispersion element, which spectrally separates the light, and through a focusing lens. The focused light can be incident on a detector array (e.g., CCD) capable of detecting the simultaneously spatially focused and spectrally diverged light from the detection regions of all the channels. Electronic signals from the detector array can provide information about the character or sequence of the DNA sample.

BRIEF DESCRIPTION OF THE DRAWINGS

The structure and manner of operation of the invention may further be understood by reference to the following description taken in conjunction with the accompanying drawings, in which identical reference numerals identify identical or similar elements, and in which.

DESCRIPTION OF THE INVENTION

Figure 1:
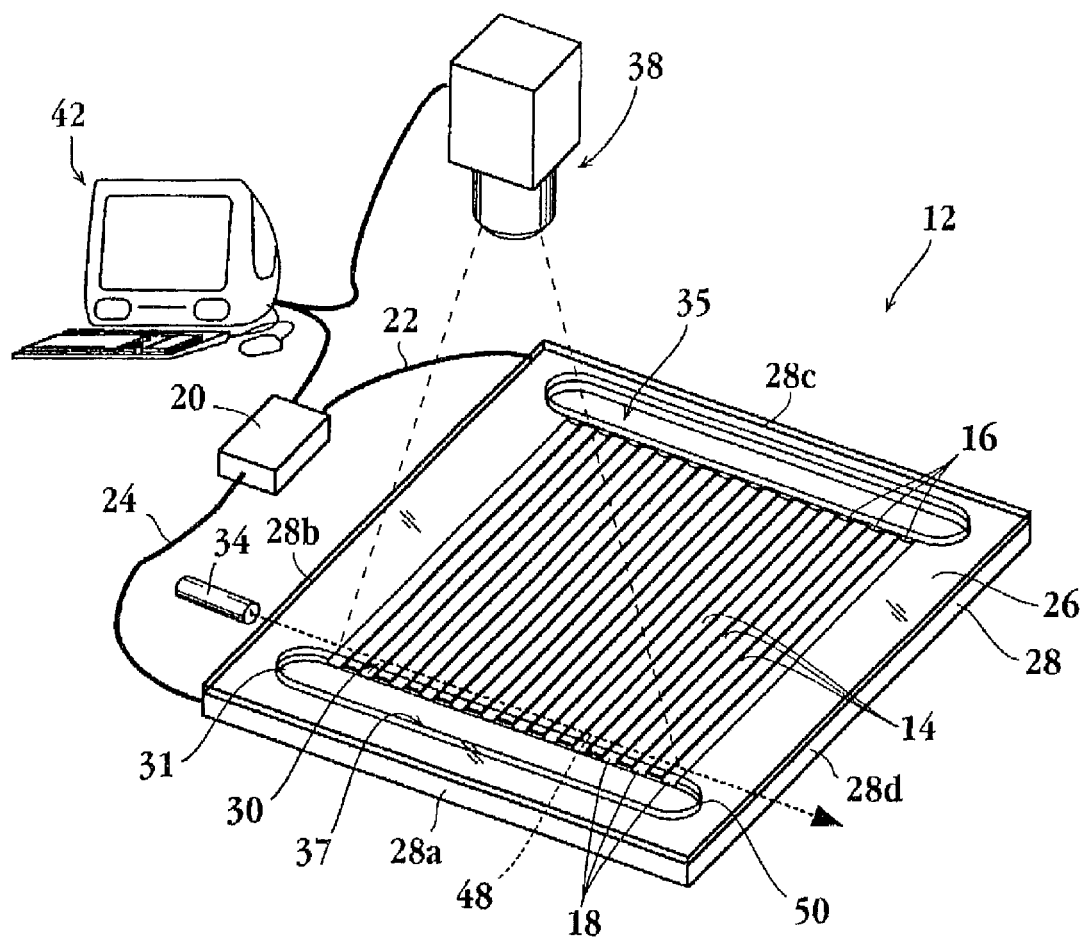
FIG. 1 is a perspective view from above of an electrophoresis system, showing a multi-channel analyte-separation device including a plurality of separation channels, a detection zone, an excitation beam source, an optical detection system, and a programmed computer control/analysis system, according to various embodiments.

Reference will now be made to various embodiments of the invention, examples of which are illustrated in the accompanying drawings. While the invention will be described in conjunction with various embodiments, it will be understood that they are not intended to limit the invention. On the contrary, the invention is intended to cover alternatives, modifications, and equivalents, which may be included within the invention as defined by the appended claims.

Aspects of the invention provide a microdevice including one or more memory structures integrated into the microdevice. Further aspects of the invention provide a sample processing station configured for reading from and/or writing/rewriting to the memory of a microdevice.

Unless stated otherwise, the following terms and phrases as used herein are intended to have the following meanings:

The term "channel" as used herein refers to an elongate, narrow passage or other structure (e.g., grooves, etc.) formed in a substrate and capable of supporting a volume of separation medium and/or buffer solution; e.g., such as is used in carrying out electrophoresis. The geometry of a channel may vary widely. For example, a channel can have a circular, oval, semi-circular, semi-oval, triangular, rectangular, square, or other cross-section, or a combination thereof. Channels can be fabricated by a wide range of technologies, including microfabrication techniques. As used herein, the term "channel" is not intended to encompass a capillary tube.

The terms "capillary" and "capillary tube" as used herein, refer to an elongated tubular or cylindrical structure defining an inner lumen. For example, a capillary can be an elongated capillary or micro-capillary tube made, for example, from fused silica, quartz, silicate-based glass, such as borosilicate glass, phosphate glass, alumina-containing glass, and the like, or other silica-like material(s). As used herein, "capillary" does not encompass a channel in a substrate such as a plate, slide, chip, wafer, or the like.

The term "channel device" refers to a substrate, such as a plate, slide, chip, wafer, or similar structure, including one or more channels (e.g., grooves); and particularly those adapted at least in part for carrying out electrophoresis. Channel devices can take the form, for example, of microfabricated devices (e.g., a grooved, etched, or fluted plate, slide, chip, wafer, or other substrate).

As used herein, the term "sample zone" or "analyte zone" refers to a collection of molecules comprising a subset of sample or analyte components having similar electrophoretic migration velocities such that the molecules of a sample zone or analyte zone migrate as a defined zone. In the limit, such a zone is made up of molecules having identical electrophoretic migration velocities. Sample zones and analyte zones are often referred to as "bands."

As used herein, the term "separation medium" or "separation matrix" refers to a medium in which an electrophoretic separation of sample components can take place. Separation media typically comprise several components, at least one of which is a charge-carrying component, or electrolyte. The charge-carrying component is usually part of a buffer system for maintaining the separation medium at a defined pH. Media for separating polynucleotides, proteins, or other biomolecules having different sizes but identical charge-frictional drag ratios in free solution, further include a sieving component. Such sieving component is typically composed of a cross-linked polymer gel, e.g., cross-linked polyacrylamide or agarose (Sambrook), or a polymer solution, e.g., a solution of polyacrylamide, hydroxyethyl cellulose, and the like (Grossman; Madabhushi).

As used herein, the term "integrated" refers to a configuration wherein memory is fabricated into the body structure of a microdevice, or is attached to the body structure, such that the memory and body structure form a single integrated unit. The attachment can be permanent, or the memory can be removably attached to the body structure. In an embodiment of the latter, the memory is securely attached to the body structure until such time that a user should decide to remove it (e.g., one or more memory chips can be removably snap-fit to appropriately configured regions of the body structure).

Various aspects of the present invention provide channel devices useful, for example, in electrophoretic separations of bio-molecules. According to various embodiments, the channel devices employ side-entry excitation geometry. Channel devices herein are to be contrasted with capillary arrangements that employ multiple capillaries (i.e., elongated tubular structures). Rather, the channel devices herein are comprised of a substrate, such as a plate, slide, chip, wafer, or similar structure, including one or more channels (e.g., grooves). In various embodiments, channel devices take the form, for example, of microfabricated devices (e.g., a grooved, etched, or fluted plate, slide, chip, wafer, or other substrate). It has previously been suggested by others that channel-device technology was not well developed enough to employ side-entry illumination (See Yeung et al, U.S. Pat. No. 5,741,411 [col. 8, lines 14-24] and U.S. Pat. No. 5,582,705 [col. 8, lines 9-19]). To the contrary, the present invention prefers the use of channel devices over multiple capillary (tube) arrangements.

In various embodiments, separation channels are formed on a glass or plastic substrate, such as a plate, slide, wafer, chip, or the like, by microfabrication techniques known in the art, e.g., photolithographical and/or wet-chemical etching procedures, laser ablation, electroforming, microcontact printing, microstamping, micromolding, microcasting, micromachining, engraving, and/or embossing techniques, to name a few. For example, Backhouse et al., Dolnik et al., and Woolley et al (each of which is incorporated herein by reference) discuss certain fabrication techniques that the skilled artisan can employ in making the devices of the present invention. In one embodiment, the separation channels are formed in a generally planar substrate comprised at least in part, for example, of an electrically insulating material, e.g., fused silica, quartz, silicate-based glass, such as borosilicate glass, phosphate glass, alumina-containing glass, and the like, or other silica-like material(s).

Various embodiments of the devices herein are particularly well suited, for example, to fluorescence detection of a fluorescent target species in a sample. According to various embodiments, channels of a channel device are arranged in a coplanar channel array. In various embodiments, the channel array includes at least about 4 (e.g., 8, 12, 16, 24, 48, 96, or more) coplanar, adjacently arranged channels. Sidewall regions of each channel include one or more transparent portions. According to certain embodiments, a transparent portion is transparent to light having a wavelength about equal to a wavelength of a beam of coherent light used to irradiate a target species in a channel. A "transparent portion" or "transparent medium" is one that transmits light with little or no attendant light scattering. For example, a transparent portion can be comprised of an optically clear glass or plastic. According to certain embodiments, the transparent portion is transparent to light having a wavelength of about 200-1500 nm; e.g., about 250-800 nm.

Together, the transparent portions define a transparent path extending through the channel array, e.g., from each channel to the next. In an embodiment, the transparent path comprises a plane extending through the channels, as is the case where the channels are fabricated entirely out of transparent material.

In certain embodiments, the transparent portions of the sidewalls exhibit little or no fluorescence when exposed to a beam of coherent light, so as to reduce or eliminate background fluorescence from the detected fluorescence. For example, the transparent portions can be selected and designed to exhibit substantially no fluorescence when exposed light having a wavelength of 200-1500 nm; e.g., about 250-800 nm. By "substantially no fluorescence" is meant that the level of fluorescence emitted by a transparent portion, if any, is less than observed background fluorescence.

According to various embodiments, detection of a target species can be effected through a transparent portion provided in an upper wall or ceiling region of a channel. Such additional transparent portion can be selected and designed to exhibit substantially no fluorescence when exposed to light having a wavelength about equal to the wavelength of light emitted by a fluorescing target species. In an embodiment, the entire channel device is constructed from a transparent, non-fluorescing material, such as fused silica. Transparent windows may alternatively be formed at or along selected regions of channels.

Instead of, or in addition to, utilizing such transparent portions, one or more sidewalls can include a translucent portion defining a translucent path extending through the array perpendicular to the channels. A translucent medium produces some light scattering when transmitting light. In certain embodiments, transparency is preferred over translucency because of greater light throughput and reduced detection S/N.

As indicated above, side-entry irradiation of target species in multiple channels can be effected through a transparent portion of a sidewall of each channel in a multi-channel array. According to various embodiments, light passes through the transparent portions in the array in a sequential manner. A coherent light source can be positioned to direct a beam of coherent light along the transparent path. A coherent light source produces light waves traveling together in phase. The light can have, for example, a wavelength of about 200-1,500 nm. For example, the coherent light source used can be a laser. An argon ion laser operating simultaneously at one or more visible lines can be used for excitation, although other light sources and wavelengths can be used. Exemplary excitation wavelengths are 488 nm and 514 nm. A pure output laser, i.e., a laser emitting light of a single wavelength, can be a useful light source. Alternatively, the wavelength of the laser can be chosen by an interference filter or a glass prism.

According to various embodiments, the beam of coherent light is focused and collimated through a collimating focusing lens interposed between the coherent light source and the channel array. For example, the collimated excitation beam can have a diameter of less than about 300 micrometers (e.g., less than about 75 or 50 micrometers) while traversing the channels in the array. In an embodiment, including an array comprising about 96 channels, the array width is less than about 1.5 cm, and a lens with a focal length of about 530 cm, e.g., about 10 cm, is used to focus and collimate the beam such that the beam diameter remains less than about 75 micrometers while in the channels.

According to various embodiments, the focused line of the laser is altered with a beam expander in order to more effectively irradiate a large number of channels. For example, the laser beam can be expanded perpendicular to the capillary array. Such lengthening or "fanning out" of the laser line can facilitate positioning of the beam so that all channels are adequately irradiated. The beam can optionally be altered or redirected, as with a mirror, filter, lens, or other optical element, prior to contacting the array. For example, mirrors can be used to provide a convenient means for adjusting the direction of the laser beam to become coplanar with the channel array perpendicular to the channels. The use of mirrors, filters, lenses, etc., or any combination thereof, is optional.

A location external to the channel array to which the transparent path may be optically coupled is to be broadly understood as any point, line, or plane external to the array, including a single pixel, linear array of pixels, or planar array (two-dimensional array) of pixels. For example, the location external to the capillary array can comprise a planar surface parallel or angled with respect to the channel array. The location external to the capillary array can include an optical detector, e.g., capable of detecting fluorescence emission from a target species in a sample in a channel. In an embodiment, the optical detector is a two-dimensional image array detector. For example, the optical detector can be a charge-coupled device (CCD) or a charge-injection device (CID).

Referring now to the drawings, FIG. 1 is a perspective view of an embodiment of an electrophoresis device, indicated generally by the reference numeral 12. Device 12 includes a plurality of separation channels, such as elongate channels 14, with each channel having an inlet end and an outlet end, as indicated at 16 and 18 respectively. A first lead wire 22 connects a power source 20 with a first electrode (not visible in FIG. 1) disposed in electrical communication with the inlet ends of the separation channels; and a second lead wire 24 connects source 20 with a second electrode (not visible in FIG. 1) disposed in electrical communication with the outlet ends of the separation channels. In operation, a voltage is applied between the first and second electrodes, and thereby along the channels, such that a sample zone is transported from the inlet ends, to the outlet ends of the channels, and through an on-channel detection zone, denoted as 30, located between the inlet and outlet ends.

In the arrangement of FIG. 1, device 12 is comprised of upper and lower plates, 26 and 28 respectively, with abutted confronting faces. As shown, lower plate includes end portions, 28a and 28c, and lateral side portions, 28b and 28d. Lower plate 28 is provided with a plurality of non-intersecting elongate grooves, each of roughly semi-circular or semi-oval cross-section, positioned at regular intervals (e.g., at a pitch of about 250 um) and extending along its upper face (e.g., for a length of about 5 cm); which grooves in part define separation channels 14. The lower face of plate 26 is substantially planar, and, when disposed against plate 28 as shown, further defines channels 14. Particularly, in the illustrated arrangement, the grooves of plate 28 define lower (floor) and sidewalls, or boundaries, of each channel 14 and the lower surface of plate 26 provides an upper wall for each channel 14.

Alternatively, both the upper and lower plates can be provided with complimentary sets of grooves that can be aligned with one another so that corresponding upper and lower grooves cooperate to define a plurality of elongate channels.

Instead of providing grooves in a lower plate which are covered by a planar lower surface of an upper plate, such as shown in FIG. 1, the device of the invention can include an upper plate with grooves formed along its lower surface, which can be placed over a planar upper surface of a lower plate (that is, essentially, the reverse of what is shown in FIG. 1). Moreover, although the device of the invention is illustrated as operating with the major planar surfaces of the plates disposed in a substantially horizontal fashion, the device instead could instead be configured to operate with the plates disposed substantially vertically, or tilted at a desired angle.

While the channels depicted in FIG. 1 are parallel to one another, it should be appreciated that other configurations are possible. In one embodiment, the channels converge toward one end of the device (e.g.; the distance separating adjacent channels (i.e., the pitch) becomes smaller along a direction towards the outlet ends). Additionally, it should be noted that the central longitudinal axes of the channels can be straight (as shown), curved, or a combination thereof. In the embodiment of FIG. 1, the flow cross-sectional area (i.e., the cross section taken perpendicular to the direction of sample migration) is substantially the same among the various channels. In particular, the channels of FIG. 1 are all of a uniform depth (measured from the lower face of the upper plate bounding the top region of the channel to the lowermost point, or floor, of the channel groove). Such uniformity can be achieved as the ordinary result of common microfabrication methods employed in constructing the device, such as etching. However, the invention additionally contemplates channels of varying depth; which can be made, for example, by use of a two stage etching process with multiple masks.

In practice, a separation medium is injected (e.g., pressure-filled or vacuum aspirated) or otherwise provided in the separation channels of the invention to effect the electrophoretic separation of the components of the sample(s). It should be noted that the present invention contemplates the use of any suitable injection techniques; e.g., without limitation, electrokinetic injections, hydrodynamic injections, cross tee injectors and double tee injectors, etc., as known and described in the art. In one preferred embodiment, the separation medium is a flowable, non-crosslinked polymer solution.

An excitation-beam source, such as 34, is provided for stimulating emission from sample zones located in detection zone 30. In an embodiment, the light source is a laser, e.g., an argon ion laser, a solid-state laser, or the like; however, any suitable beam source can be used. As described in more detail below, in an embodiment of the present invention, an excitation-beam pathway or path extends through detection zone 30, along which an energy beam 48 generated by the beam source can pass. Such pathway is located between the inlet and outlet ends and extends along a plane defined by the channels (i.e., the pathway is coplanar with the plane of the channels). In an embodiment, the beam pathway is perpendicular to the direction of sample migration across the detection chamber, but this is not critical to the invention (i.e., the pathway can approach at an angle with respect to the direction of sample migration). What is important in this embodiment is that a beam passing along the pathway is capable of simultaneously exciting plural sample zones in respective (different) channels.

In various embodiments, such as shown in the arrangement of FIG. 1, the beam enters a lateral side 28b of lower plate 28, passes through plate 28 (including each of channels 14), and exits at an opposite lateral side 28d of plate 28. In other embodiments, a laser dump or sink can be incorporated in the plate, e.g., proximate a region of side 28d, whereat the beam can terminate after passing through the channels.

As previously mentioned, a first electrode (not visible in FIG. 1) is in electrical communication with inlet ends 16 of separation channels 14. During operation of device 12, the first electrode is maintained at a first voltage V1 using power source 20. Electrical communication between the first electrode and the inlet ends of the separation channels can be established, for example, by providing an electrically conductive solution in a reservoir/loading region 35 of device 14 so that both the inlet ends of the channels and the first electrode are in contact with the conductive solution.

With continued reference to FIG. 1, each of outlet ends 18 communicates a respective channel 14 with a second reservoir 37, which reservoir is located proximate the outlet ends. The second electrode (not visible in FIG. 1) is in electrical communication with outlet ends 18 of separation channels 14. During operation of device 12, the second electrode is maintained at a second voltage V.sub.2, also using power supply 20. Preferably, electrical communication between the second electrode and second reservoir 37 is established by providing an electrically conductive solution in second reservoir 37 such that the second electrode and outlet ends 18 are in contact with the conductive solution.

The electrodes used in the device may be formed from any electrically conducting materials. Preferably, the electrodes are made from a chemically inert material, e.g., platinum, gold, stainless steel, or other relatively inert conductive material. In accordance with one embodiment of the present invention, platinum electrodes are fabricated on the top or bottom plate by RF sputtering and photolithography before the top plate is bonded to the etched bottom plate.

The electrically conductive solution used to establish electrical continuity throughout the system can be any fluid capable of transporting an electrical current. For example, the conductive solution can be an ionic solution, e.g., an aqueous solution containing a dissolved salt. In various embodiments, the conductive solution includes a buffer for stabilizing the pH of the solution. According to certain embodiments, the ionic composition of the conductive solution is the same in the separation channels, each of the electrode reservoirs, and the detection chamber.

To facilitate optical detection of sample zones in the detection zone 30, part or all of upper plate 26 covering detection zone 30 can be formed from a material which efficiently transmits light (i.e., an optically clear material), e.g., glass, quartz, clear plastic, and the like. In addition, to facilitate the introduction of an excitation light beam 48 into the detection zone to excite fluorescence of sample zones therein, part or all of the plate 28 along a region between the beam source 34 and the endmost channel 14 closest thereto can be formed from a material which efficiently transmits light. In various embodiments, the light-transmitting material does not significantly scatter light and has little intrinsic fluorescence.

Further in the embodiment of FIG. 1, a detector 38 is provided for detecting sample zones passing through the detection zone 30. The detector can be any type of detector for detecting emission of any type radiation, e.g., radioactivity, fluorescence, phosphorescence, chemi-luminescence, and the like. In an embodiment, detector 38 is capable of detecting fluorescence from a plurality of locations independently and simultaneously, e.g., a CCD camera, an array of photomultiplier tubes, a diode array, and the like. As illustrated in FIG. 1, detector 38 can be connected to a computer 42 to store, analyze, and display data collected by the detector and/or to control the operation of the detector and other aspects of the device, as desired. For example, computer 42 can be programmed to control power source 20 and/or beam source 34.

It should be appreciated that, in regions of the device where it is not required or desired that radiative emission should be able to pass through, non-optically clear materials may be used, e.g., polymeric materials such as Teflon, silicone, and the like. Of course, the detection zone, as previously mentioned, preferably permits light to pass from each channel to the next channel, and to the detector.

The electrophoresis apparatus of the present invention can also include one or more additional elements typically used to conduct a capillary electrophoresis process, e.g., a temperature control device for controlling the temperature of the separation channels. Details of these and other common features of an operable capillary electrophoresis device can be found in any number of available publications, e.g., Capillary Electrophoresis Theory and Practice, Grossman and Colburn, eds., Academic Press (1992).

Various embodiments provide for reduced crosstalk, while facilitating excitation and detection. Certain embodiments, for example, utilize bandpass filters that transmit light only within a defined spectral band. For example, an excitation filter can be employed (e.g., coated upon or fixed to regions of the lower plate) that allows only light which excites a reporter of interest to strike the sample. An emission filter can be employed (e.g., coated upon or fixed to regions of the upper plate) that allows the fluorescence from the sample to pass to a detector and blocks stray light from the light source or interfering components in the sample.

Figure 2A:
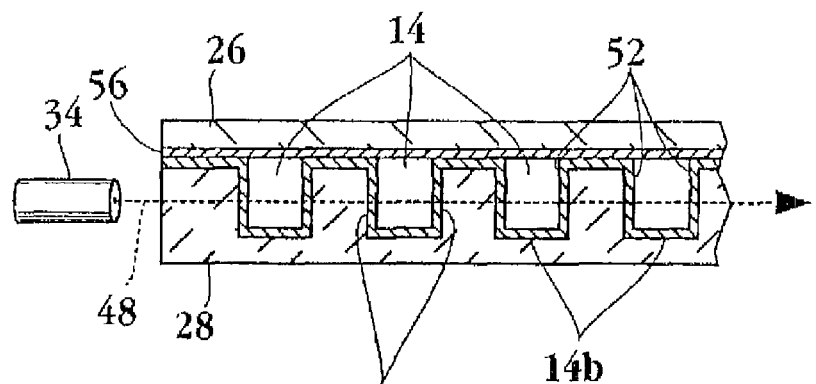
FIGS. 2A, 2B, and 2C are partial, cross-sectional views of multi-channel analyte-separation devices, according to various embodiments.
Figure 2B:
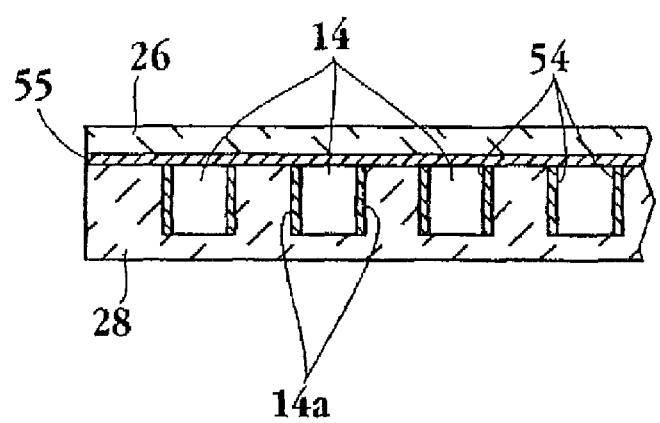
Figure 2C:
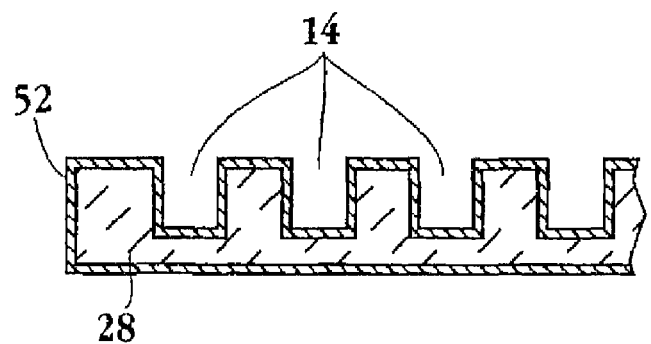
Figure 3A:
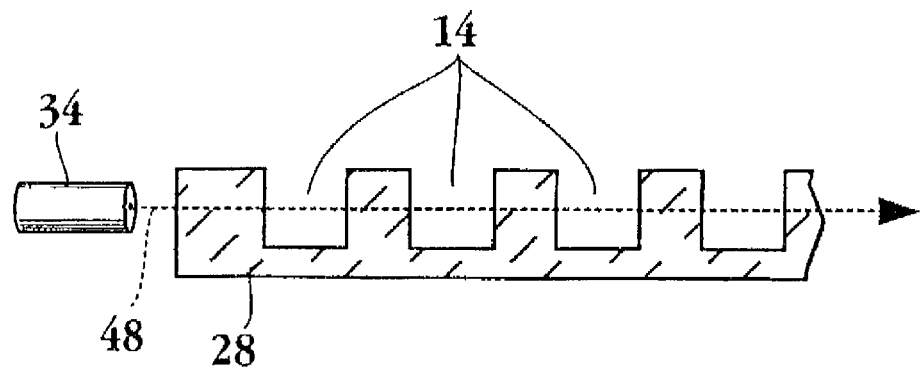
FIGS. 3A, 3B, and 3C are cross-sectional views of substrates with channels formed therein having various geometries, according to certain embodiments.
Figure 3B:
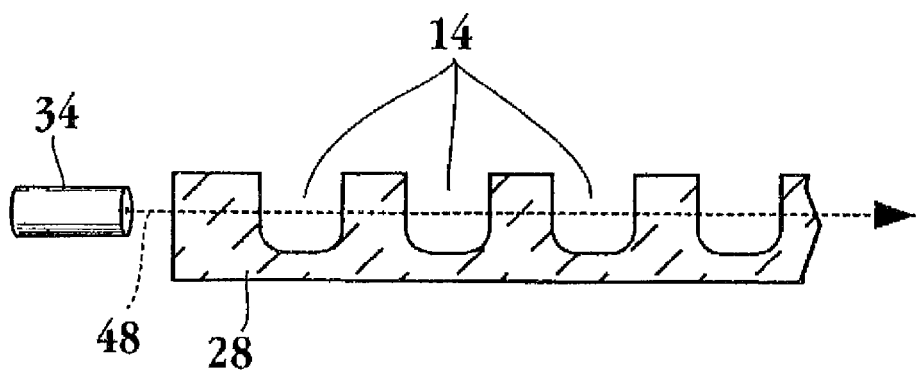
Figure 3C:
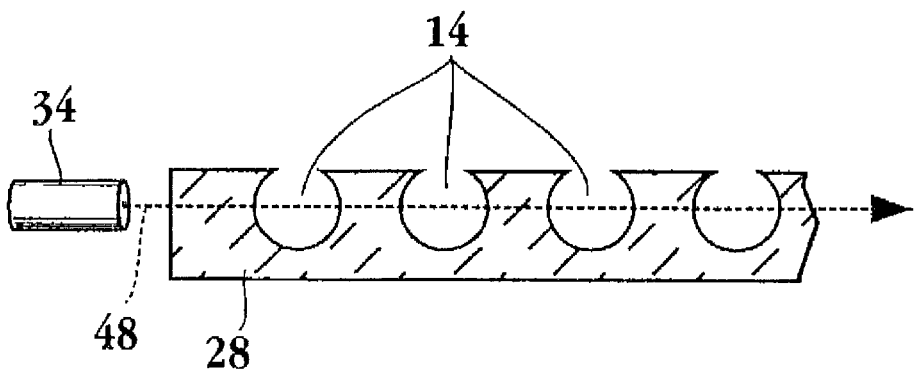

In an exemplary arrangement, as depicted in the sectional view of FIG. 2, a lower glass or plastic plate 28 is provided with spaced-apart etched channels 14. While each channel 4 is shown having vertical sidewalls 14a and a flat bottom or floor region 14b, which meet at ninety-degree angles, other channel geometries can be employed (see, e.g., FIG. 3). The sidewalls 14a of the channels have bandpass characteristics that permit passage only of the excitation (laser) beam 48 through the device (e.g., a coating material, as at 52, applied to the channel sidewalls 14a and, optionally, the floor regions 14b; or micro-optical elements 54 attached on each sidewall 14a (see FIG. 2B); or the whole lower etched plate (including the channels in their entireties) can be coated with a bandpass coating permitting only excitation light to pass (see FIG. 2C)). An upper or cover plate 26, overlaid over the channels 14, can be provided with bandpass characteristics that let only sample emission (e.g., fluorescence) to pass through (and not excitation beam wavelengths). For example, a bandpass coating material, as at 56 (FIG. 2A), can be applied to a face or face regions of the upper plate 26 that confront the lower plate 28 and channels 14, at least along regions along the detection zone. Or, a micro-optical bandpass element, such as element 55 in FIG. 2B, can be attached to the side of upper plate 26 confronting lower plate 28. By these or similar arrangements, excitation light is permitted to pass laterally through the device in a side-entry, on-channel configuration (with light of other bandwidths being substantially excluded), while fluorescent emission from sample zones is permitted to pass out of the channel to a detector (with light of other bandwidths being substantially excluded).

A number of commercial entities produce a wide range of coating technology products that can find use with the teachings herein, including bandpass filters, beamsplitters, reflectors and collectors, sputtered metals, etc. (For example: Seoul Precision Optics Co.; GM Vacuum, A Division of Navitar Coating Labs; Optical Coating Laboratory, Inc.; and Guernsey Coating Laboratories Inc.).

Optical elements and coatings useful in connection with the present teachings are described, for example, in U.S. Pat. Nos. 3,466,120; 6,112,005; 5,872,655; 4,663,557; 6,100,541; each of which is expressly incorporated herein by reference.

Figure 4:
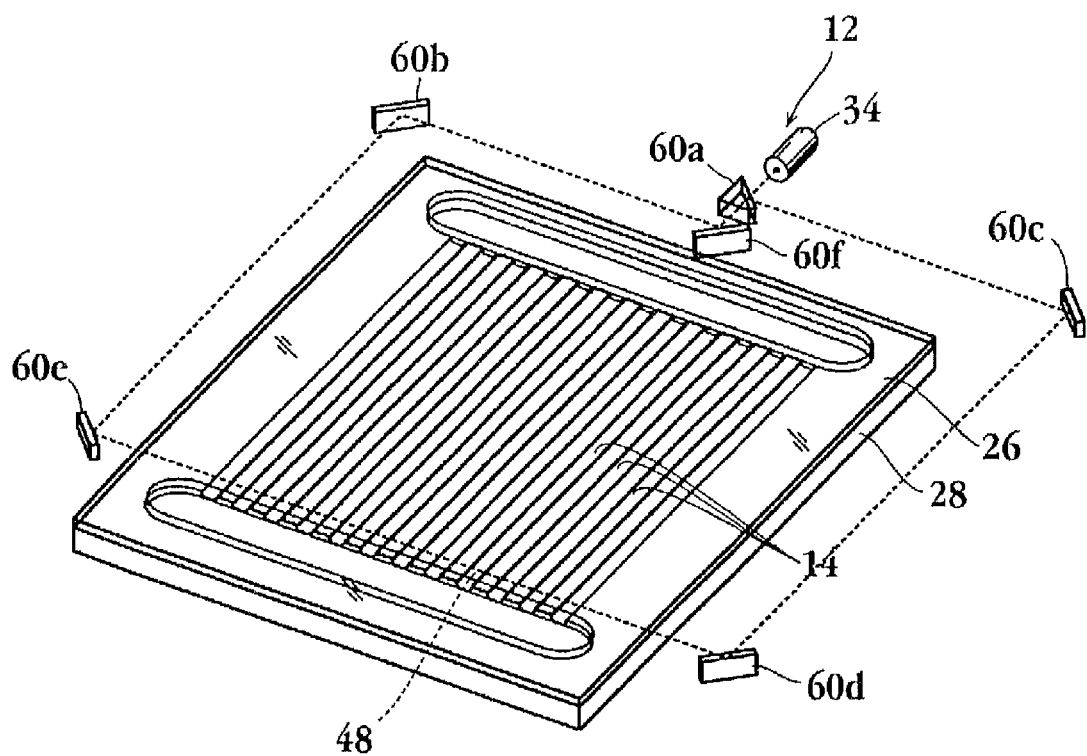
FIG. 4 is a perspective view from above of an electrophoresis system, including a multi-channel analyte-separation device including a plurality of separation channels, an excitation beam source, and optics directing an excitation beam for entry into the channel device from each lateral side thereof, according to various embodiments.

According to various embodiments, an excitation beam of light is directed toward the array from each lateral side of the device. For example, two lasers can be employed, one on each side of the device. Or, as depicted in FIG. 4, a single laser source 34 can be employed in combination with appropriate beam splitting and directing optics, such as at 60a-60e, so that light enters the array from each lateral side of the device.

It should be noted that, in some instances, one of skill in the art may choose to use less than all of the channels provided by the device of the invention to conduct separations. For instance, the left- and right-endmost channels might not be loaded with samples, while the remaining channels are so loaded; or, every other channel might be utilized, with the intervening channels remaining unused.

Various embodiments of a channel device include a substrate, with a plurality of channels formed in the substrate. Each channel includes an inlet end and an outlet end. The channels are disposed in spaced relation relative to one another, with each adjacent pair of channels being separated by a respective portion of the substrate that includes at least a region that is transparent. An excitation-beam source is adapted to direct a beam of coherent light along a beam path that intersects each of the channels at a region between the inlet and outlet ends, and further intersects the transparent region of the substrate separating adjacent pairs of channels.

According to certain embodiments, each channel includes opposed sidewalls with portions that are substantially parallel to one another. The parallel portions are at least in part transparent, and the beam path extends through the transparent, parallel portions. Such construction can be useful to avoid or reduce loss of light intensity as the beam travels through the device, from channel to channel.

According to various embodiments, a typical microdevice includes a substrate or body structure that has one or more microscale sample-support, manipulation, and/or analysis structures, such as a channel, well, chamber, reservoir, valve or the like disposed within it. As used herein, "microscale" refers to a fluid channel or conduit that has at least one cross-sectional dimension, e.g., width, depth or diameter, of no greater than about 1 micrometer. In various embodiments, such channels have at least one cross-sectional dimension of no greater than 750 micrometers, and in certain embodiments, from 1 to 500 micrometers (e.g., between 5 to 250, or between 5 to 100, micrometers). In one embodiment, a microscale channel has at least one cross-sectional dimension of between about 10-75 micrometers. With respect to chambers or wells, "microscale," as used herein, refers to structures configured to hold a small (micro) volume of fluid; e.g., no greater than 250-300 μl. In various embodiments, such chambers are configured to hold no more than 100 μl, no more than 75 μl, no more than 50 μl, no more than 25 μl, no more than 1 μl, or no more than 50 nl (e.g., about 30 nl).

A micro-device can be configured in any of a variety of shapes and sizes. In various embodiments, a microdevice is generally rectangular, having a width dimension of no greater than about 15 cm (e.g., about 2, 6, 8 or 10 cm), and a length dimension of no greater than about 30 cm (e.g., about 3, 5, 10, 15 or 20 cm). In other embodiments a microdevice is generally square shaped. In still further embodiments, the substrate is generally circular (i.e., disc-shaped), having a diameter of no greater than about 35 cm (e.g., about 7.5, 11.5, or 30.5 cm). The disc can have a central hole formed therein, e.g., to receive a spindle (having a diameter, e.g., of about 1.5 or 2.2 cm). Other shapes and dimensions are contemplated herein, as well.

Chip, wafer, and plate devices (e.g., genetic analysis microdevices, microchannel electrophoresis devices, per chips, μTAS devices, lab-on-a-chip systems, sample preparation/cleanup devices, etc.), spinning disc substrates (e.g., those developed by Gyros and Gamera), and biomolecule array chips (e.g., those developed by Hyseq and Affymetrix) have been the subjects of intensive R&D efforts. Such devices generally permit many operations to be performed at once on a large number of samples (e.g., tens, hundreds, thousands, tens of thousands, or more), with the samples all being the same or substantially the same, all being different from one another, or some combination thereof. The present invention combines such structures with a portable or small-scale memory format; and in various embodiments, a readable, writable, and/or rewritable memory (or simply, a "rewritable" memory).

The present teachings are particularly well suited for microfluidic devices. The term "microfluidic" refers to a system or device having channels, chambers, wells, and/or reservoirs (e.g., a network of chambers and/or wells connected by channels) for supporting or accommodating very small (micro) volumes of fluids, and in which the channels, chambers, wells, and/or reservoirs have microscale dimensions. See, e.g., U.S. Pat. Nos. 6,132,685, 6,103,199, 6,054,277, and 6,033,546; and EP 1003759; and WO 0126812, WO 0076662, and WO 9850154; each incorporated herein by reference.

A variety of memory structures permitting integration into a microdevice can be utilized herein, e.g., integrated circuit memories, optical memories, thin film semi-conductor memories, ferromagnetic memories (e.g., magnetic stripe memories; see, e.g., U.S. Pat. No. 4,281,396; incorporated herein by reference), molecular memories (see, e.g., U.S. Pat. No. 6,256,767, incorporated herein by reference), and biomolecular memories (e.g., storage devices based upon conformational states of organic molecules, such as bacteriorhodopsin (BR); see, e.g., Birge et al., Biomolecular electronics: Protein-based associative processors and volumetric memories, J. Phys. Chem. B. 103, 10746-10766 (1999); and Birge, R., "Protein-Based Three-Dimensional Memory," American Scientist, July-August 1994, pp. 348-355; each incorporated herein by reference), etc.

Thanks in large part to the widespread acceptance and use of digital cameras, mobile computing devices, personal music players, etc., small-format memory devices have become well developed in recent years. Memory cards, such as flash cards, and portable discs, such as readable-writable-rewritable CDs and DVDs, are gaining wide use. These, and other, small-format memory devices can be employed herein.

According to various embodiments, a microdevice is provided with, for example, a memory of a type that can store information even when there is no power supplied to it. For example, a microdevice can include a flash memory; e.g., the flash technology utilized in commercial products such as CompactFlash™ (by SanDisk), MemoryStick™ (by Sony), SmartMedia™ (by Toshiba), etc. In brief, a typical flash memory, for example, includes flash memory chips and a microcontroller chip that manages the storage of digital information (images, data, voice, etc.) and electronic interfacing flash memory is a nonvolatile silicon memory, meaning that no battery power is required to keep the digital information stored on the card literally for hundreds of years without deterioration of information quality. See, for example, U.S. Pat. Nos. 6,252,791, 5,172,338, 5,663,901, 5,747,359, 5,887, 145; and 6,199,122; each of which is incorporated herein by reference.

It should be appreciated that flash-memory devices are merely one category of memory that can readily be incorporated into a microdevice, as taught herein, and that the invention is not limited to flash memory, but includes a variety of small-format or portable memory structures capable of being integrated into a microdevice.

In various embodiments, the memory is adapted for storing binary coded information (see, e.g., U.S. Pat. Nos. 4,905,189, 4,477,739, 5,923,583; 4,831,584; each incorporated herein by reference).

An integrated memory, as contemplated herein, can be configured with a variety of storage capacities. In various embodiments, for example, a microdevice of the invention includes an integrated memory having a storage capacity of at least 250 kilobytes (kb), at least 500 kb, at least 750 kb, at least 1 megabyte (Mb), at least 10 Mb, at least 100 Mb, at least 250 Mb, at least 500 Mb, and/or at least 1 Gigabyte (Gb), or higher.

Microscale sample-support, manipulation, and/or analysis structures (e.g., channels, chambers, wells, reservoirs, valves, micro-electronics such as electrodes, etc.) can be formed in or on a substrate, such as a plate, slide, wafer, chip, disc, or the like, by fabrication techniques known in the art, e.g., photolithographical and/or wet-chemical etching procedures, laser ablation, electroforming, microcontact printing, microstamping, micromolding, microcasting, micromachining, engraving, and/or embossing techniques, to name a few. For example, Backhouse et al., DNA sequencing in a monolithic microchannel device, Electrophoresis 2000, 21, 150-156; Dolnik et al., Capillary electrophoresis on microchip, Electrophoresis 2000, 21, 41-54; Woolley et al., Ultra-high-speed DNA fragment separations using microfabricated capillary array electrophoresis chips, Proc. Natl. Acad. Sci., vol. 91, pp. 11348-11352, November 1994; and Madou, Fundamentals of Microfabrication, CRC Press, Boca Raton, Fla. (1997) (each of which is incorporated herein by reference) discuss certain microfabrication techniques that the skilled artisan can employ in making microdevices.

In various embodiments, separation channels are formed in a generally planar substrate comprised at least in part, for example, of an electrically insulating material, e.g., fused silica, quartz, silicate-based glass, such as borosilicate glass, phosphate glass, alumina-containing glass, and the like, or other silica-like material(s). According to some embodiments, separation channels are formed in a plastic substrate.

One suitable channel microdevice for use in the present invention is the Standard Microfluidic Chip (Simple Cross, MC-BF4-SC) from Micralyne Inc. (Edmonton, Alberta, Canada). Multiple cross-channel or other channel arrangements can be provided on a single chip or plate, as desired.

A channel microdevice, as contemplated herein, can include no more than one channel, or can include a plurality of channels, e.g., at least 5, 10, 15, 20, 25, or more channels. In an embodiment, a microdevice for analyte separation includes at least 5, 10 or 15 separation channels.

Figure 5:
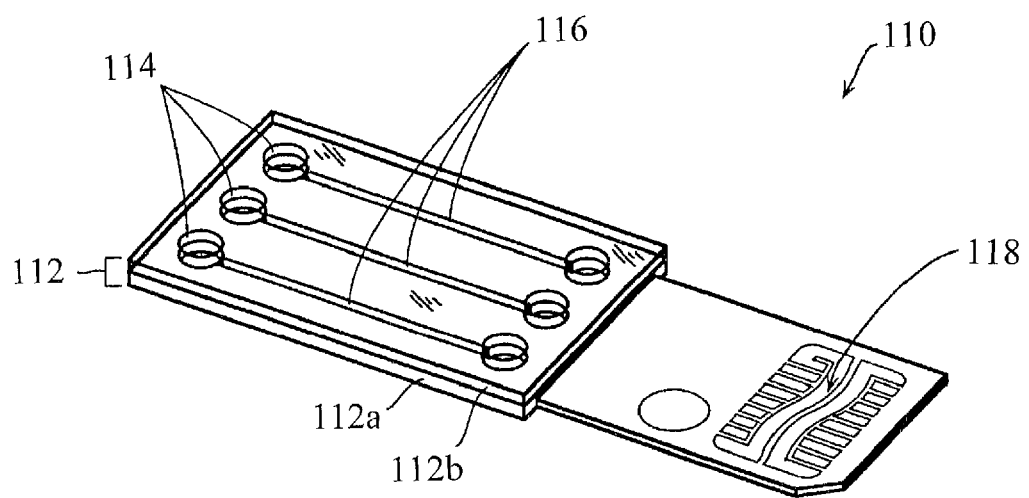
FIG. 5 is a perspective view of a microdevice including an integrated memory, in accordance with the teachings herein.

In the exemplary arrangement of FIG. 5, a microdevice 110 comprises a substrate (or body) 112 in which sample chambers 114 and channels 116 are formed (e.g., microfabricated), with a chamber or reservoir provided in fluid communication with each end of each channel. More particularly, substrate 112 is comprised of lower and upper plates, 112a and 112b respectively, with abutted confronting faces. Lower plate 112a is provided with elongate grooves, each of roughly semi-circular or semi-oval cross section, that in part define boundaries for channels 116. The lower face of upper plate 112b is substantially planar, and, when disposed against lower plate 112a as shown, further defines boundaries for channels 116. Particularly, in the illustrated arrangement, the grooves of plate 112a define lower (floor) and sidewalls or boundaries of each channel 116 and the lower surface of plate 112b provides an upper wall or ceiling (boundary) for channels 116. Through-holes can be formed through upper plate 112b to provide access to, and to define in part, the chambers 114.

Lower plate 112a of substrate 112 includes a region, as at 118, incorporating readable-writable-rewritable memory, such as flash memory. Memory region 118, in this embodiment, is configured as an outwardly extending projection, in the plane of lower plate 112a, so that upper plate 112b does not cover it. The projection can be configured in a variety of ways. In various embodiments, for example, the projection is provided with the shape of a standard PCMCIA card (also known as a PC card).

Figure 6:
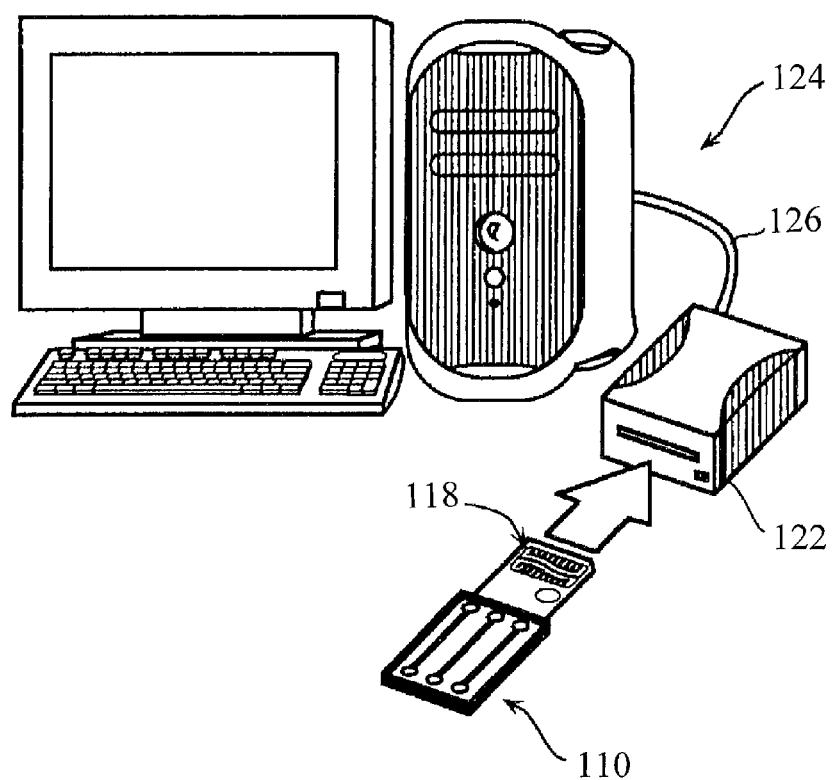
FIG. 6 is a perspective view of a microdevice including a memory region configured for insertion into a computer-connected reader-writer unit, in accordance with the teachings herein.

According to various embodiments, and with reference to the exemplary arrangement of FIG. 6, the memory region 118 of a microdevice 110 can be configured so as to be insertable into a reader-writer unit 122. The reader-writer unit 122 can be adapted for communication with a computing device, such as shown at 124, via a USB or FireWire connection 126. The memory can be written to before, during and/or after processing.

Small-format memory reader-writer units are well known (see, e.g., U.S. Pat. Nos. 6,149,058; 6,125,405; 6,223,984; JP 10320508; and WO 0067098; each incorporated herein by reference). Such known units can readily be adapted for use herein.

Figure 7:
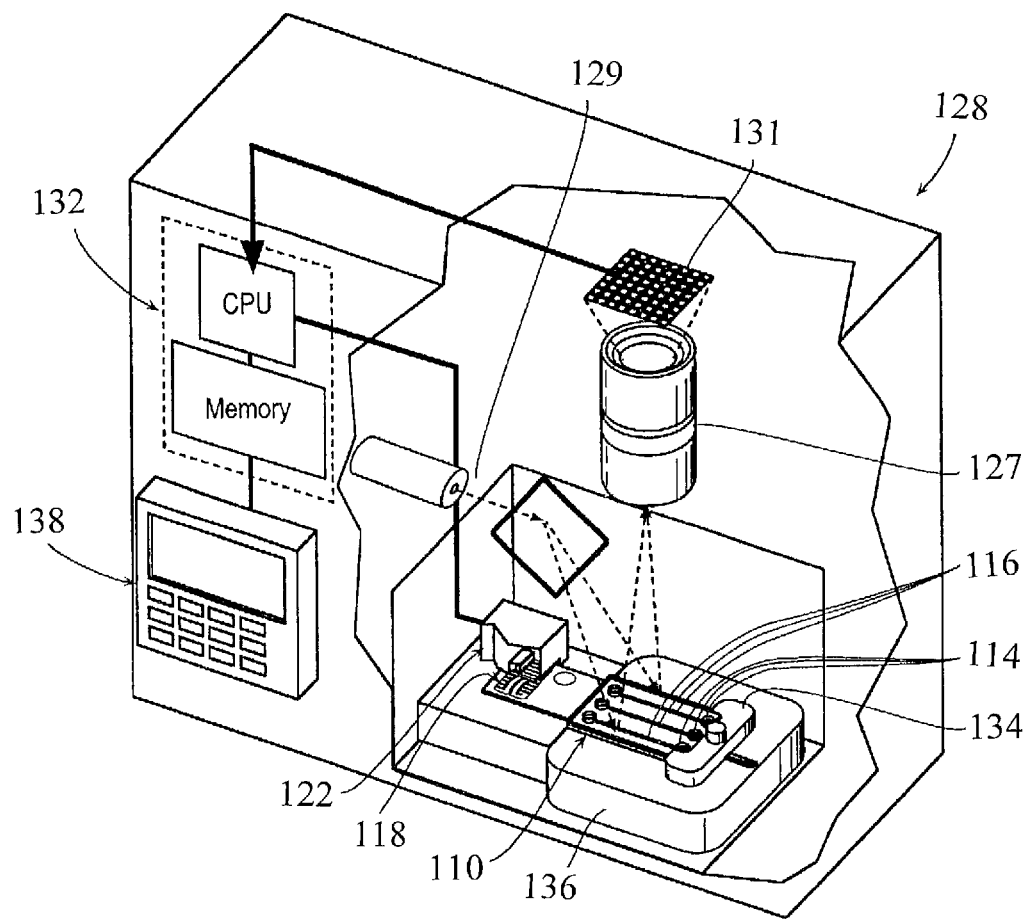
FIG. 7 is a partially schematic, perspective view, with portions broken away, of a reader-writer unit incorporated in a sample-processing station, permitting data to be read, written, and/or rewritten while a microdevice is operably mounted in the station, in accordance with the teachings herein.

According to various embodiments, and with reference to the exemplary arrangement of FIG. 7, a reader-writer unit 122 is incorporated in an apparatus or station 128 configured to carry out sample processing, such as an automated electrophoresis apparatus, so that data can be read, written, and/or rewritten while a microdevice 110 is operably mounted in the processing station 128. The processing station 128 can include integrated computing capabilities 132 programmed for receiving and processing data (alternatively, or in addition, the station 128 can be operably linked to an external computing device, such as a Macintosh or PC, and/or to a display-capable input-output device). In the illustrated embodiment, a human interface device is provided comprising an externally accessible keypad input/output unit with an LCD display, shown at 138. A variety of information, such as results or output generated from use of the station, can then be written to the integrated memory 118 of the microdevice 110. If desired, the microdevice can be transported to another computer, computing-capable processing station, or other desired location, where the stored information can be accessed, etc. Certain embodiments contemplate storing the microdevice in a safe place, so as to archive information held in the integrated memory.

In some embodiments, a microdevice is configured as a single or limited-use, disposable unit.

Various embodiments are particularly adapted to biomolecule (e.g., DNA, RNA, etc.) sequence or other analysis methods, in which each of a plurality of different fragment types is labeled with a spectrally distinctive fluorescent dye. For example, with continued reference to FIG. 7, processing station 128 can include a support 134 for mounting a microdevice 110 (here, the microdevice being a multi-channel electrophoresis device having a plurality of electroseparation channels). A thermal control module 136, e.g., Peltier-effect heat-transfer devices, is provided for regulating the temperature of the microdevice 110. A laser 129 is adapted to direct an excitation beam of light at a detection zone at a location along one or more separation channels 116 of the microchannel electrophoresis device 110. The excitation beam excites the dyes to emit light. Emitted light from sample zones passes through a collection lens, through a laser light filter, and through a focusing lens, indicated collectively at 127. The focused light is incident on a detector array 131 (e.g., a CCD) capable of detecting the emissions from the detection zone. Electronic signals from the detector array can provide information about the character or sequence of the biomolecule sample. Such information can be written by a reader=writer unit 122 to an integrated memory 118 of the device 110.

In one arrangement, two programs are installed on the computing portion 132 of the processing station 128, or on the linked computer, that can collect and analyze data produced by a micro-channel plate sequencer: (i) a data collection program ("Data Collection") and (ii) a sequencing analysis program ("Analysis"). Data Collection processes the information as it is generated and plots the four different emission signals (corresponding to the four nucleotides) over time during runs. After the runs are finished, the Data Collection program launches the Analysis program. Analysis integrates the raw data, normalizes the spacing, enhances the signal peaks, and uses this information to determine the parameters for calling the bases. The analyzed data are re-plotted together as a series of color peaks representing the nucleotide sequence (i.e., a chromatogram or electropherogram). The results are stored in a Sample File, which includes the raw data, the chromatogram, the nucleotide sequence, and the file information entered by the user. A second file that contains the sequence as text only is also generated for each sample. This sequence text file is suitable for use in other applications (e.g., database searches). See Hagemann et al., ABI Sequencing Analysis, Molecular Biotechnology, Vol. 13, 137-152 (1999); incorporated herein by reference. Any one or more of the files can be written to the memory region 118 of the microdevice 110.

It should be appreciated that the memory of the microdevice can store a variety of types of information, including software applications and/or operation instructions that can be loaded to, and executed by, a computing device such as a computing capable processing station or a desktop computer. In embodiments employing a rewritable storage medium, the stored information can reflect, for example, changes in, or processing steps performed on, one or more samples; sample lineage; plate creation; sample logging; location management; etc.

Optionally, a microdevice including an integrated memory can further include an integrated microprocessor for executing instructions (code) on-board. In various embodiments, in addition to readable-writable-rewritable memory, the microdevice further includes integrated memory storing one or more software applications and/or operating instructions that can operate on or otherwise utilize information (e.g., data) written to the readable-writable-rewritable memory of the device. The additional memory can also be readable-writable-rewritable memory, or it can be read-only memory (ROM).

Figure 8:
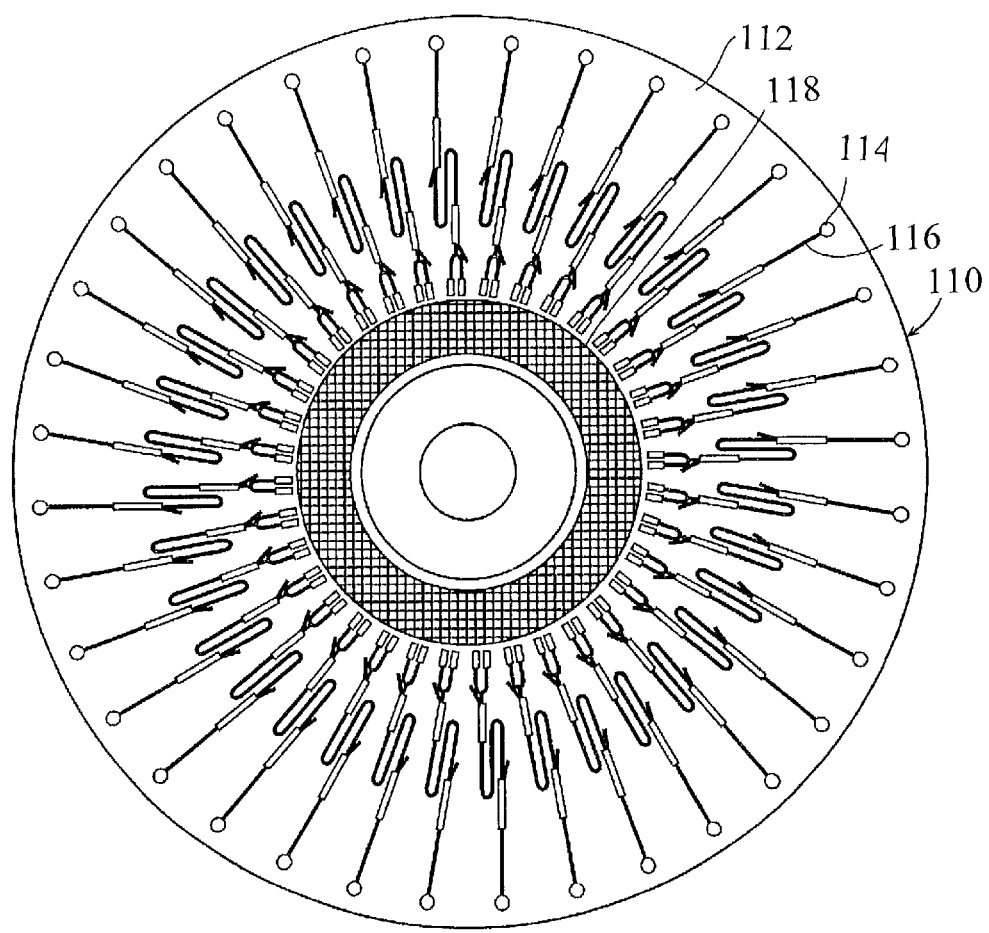
FIG. 8 is a partially schematic view of one face of a disc-type microdevice including a plurality of microfluidic structures, such as channels, chambers, etc., and a readable-writable-rewritable memory region, in accordance with the teachings herein.

In a spinning disc microdevice, an example of which is indicated at 110 in FIG. 8, a region of a disc-like substrate 112 is configured as a readable, writable, re-writable memory 118 (e.g., employing, for example, memory structures as used in CDs or DVDs). Information can be read, written and/or rewritten as the device is spinning. This can take place before, during and/or after sample processing. While exemplary channel 116 and chamber 114 structures are shown in FIG. 8, it should be appreciated that a variety of microscale structures can be utilized.

A variety of spinning disc substrates can be utilized herein. For example, micro-machined CD-type biomedical devices have been developed that may be used, for example, to analyze blood gases and blood electrolytes. Machining options for fluidic channels with diameters greater than 80 µm include direct CNC machining in plastic and plastic molding from a metal master (itself made by CNC machining). With dimensions below 80 µM, lithography techniques can be used. In some such devices, the intelligence in the structure resides in the dependence of the opening of various valves on rotation speed; the faster the disc spins, the smaller the capillaries that can be accessed by the fluids. The operating principles of certain centrifugal-based fluidic platforms are described in more detail, for example, in WO 0040750, WO 0147638, and WO 9853311; each incorporated herein by reference.

Reader-writer units and readable-writable-rewritable optical media, such as CD (e.g., CD-RW) and DVD (e.g., DVD-RW) type media, are well known (see, e.g., U.S. Pat. Nos. 5,459,707; 5,508,988; 5,465,245; 6,266,303; 5,514,440; EP 0871160; EP 0880780; EP 1091358; each incorporated herein by reference). Such known units and media can readily be adapted for use herein.

Figure 9:
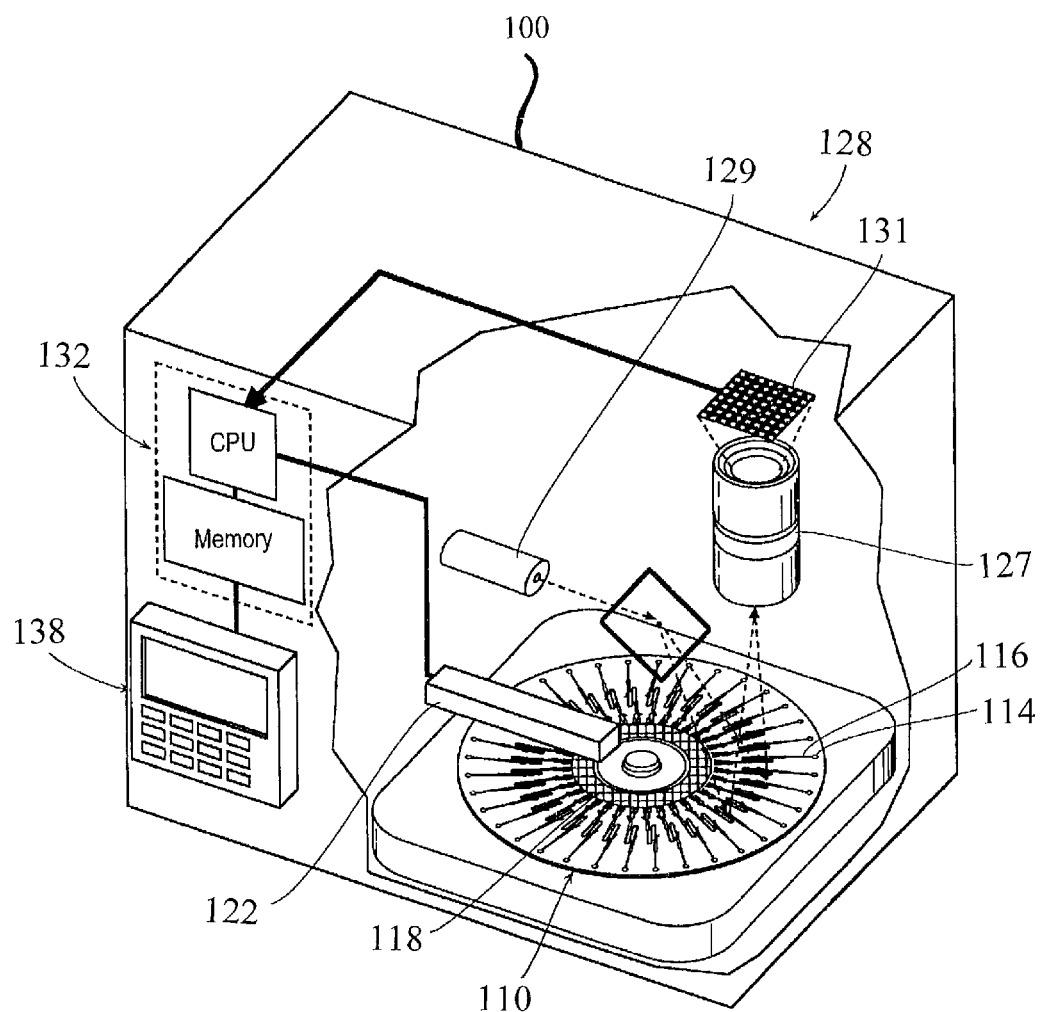
FIG. 9 is a partially schematic, perspective view, with portions broken away, of a reader-writer unit incorporated in a sample-processing station, permitting data to be read, written, and/or rewritten while a spinning-disc microdevice is operably mounted in the station, in accordance with the teachings herein.

FIG. 9 is a partially schematic, perspective view, with portions broken away, of a reader-writer unit 122 incorporated in a sample-processing station 128, permitting data to be read, written, and/or rewritten while a spinning-disc microdevice 110 is operably mounted in the station. Other components shown in FIG. 9 are substantially as described with respect to FIG. 7.

It is contemplated that a variety of types of microdevice can be configured with a readable-writable memory, in accordance with the teachings herein. For example, per-capable microdevices (such as disclosed in WO 0134842; U.S. Pat. Nos. 6,261,431; 6,203,683; each incorporated herein by reference); electrophoresis microdevices (such as disclosed in U.S. Pat. Nos. 6,261,430; 6,045,676; and pending U.S. patent application Ser. No. 08/726,093 filed Oct. 4, 1996; each incorporated herein by reference); polynucleotide array microdevices (e.g., the GeneChip™ from Affymetrix, the HyChip™ from Hyseq, and devices such as disclosed in U.S. Pat. Nos. 5,445,934; 5,837,832; EP 1047794; each incorporated herein by reference); concentration, purification and/or clean-up microdevices (such as disclosed in U.S. Provisional Patent Application Ser. No. 60/288,268 filed May 2, 2001; U.S. Provisional Patent Application Ser. No. 60/318,269 filed Sep. 7, 2001; U.S. Pat. No. 5,726,026; and WO 9933559; each incorporated herein by reference); spinning-disc-type microdevices (such as disclosed in WO 0040750, WO 0147638, and WO 9853311; each incorporated herein by reference); µTAS devices (such as disclosed in U.S. Pat. Nos. 6,194,900; 5,571,410; WO 0058724; each incorporated herein by reference); microelectromechanical system (MEMS) devices (such as disclosed in U.S. Pat. Nos. 6,116,863; 5,909,069; 5,710,466; and 5,655,665; each incorporated herein by reference); to name a few.

All publications and patent applications referred to herein are hereby incorporated by reference to the same extent as if each individual publication or patent application was specifically and individually indicated to be incorporated by reference.

Those having ordinary skill in the electrophoresis art will clearly understand that many modifications are possible in the above preferred embodiments without departing from the teachings thereof. All such modifications are intended to be encompassed within the following claims.

The invention claimed is:

1. A biomolecule sequence analysis system, comprising:
   an enclosure;
   a transportable microdevice disposed in the enclosed and further comprising a substrate constructed to support at least one biomolucule sample, the biomolecules sample comprising a sequence;
   one more biomolecule sample manipulation structures in the substrate, the sample manipulation structures configured to provide migration and separation of the biomolecules in the substrate;
   a read-write memory structure integrated into the substrate;
   a detector disposed in the enclosure and operatively positioned with respect to the substrate, the detector being adapted to generate electronic signals in response to fluorescent emissions from the one or more biomolecules separated in the substrate;
   a computing portion disposed in the enclosure and in the electrical communication with the detector, the computing portion comprising one or more programs installed thereon; and a reader-writer unit disposed in the enclosure and adapted for communication with the read-write memory structure in the substrate;

wherein the computer portion is programmed by the one or more programs to collect and analyze the electronic signals generated by the detector and determine the biomolecule sequence.

2. The biomolecule sequence analysis system of claim 1, wherein the sequence comprises DNA sequence information.

3. The biomolecule sequence analysis system of claim 1, wherein each of the one or more sample manipulation structures comprises a microscale sample manipulation structure.

4. The biomolecule sequence analysis system of claim 2, wherein the reader-writer unit is configured to write the DNA sequence information to the integrated memory.

5. The biomolecule sequence analysis system of claim 1, wherein the sequence comprises a sequence of nucleotides.

6. The biomolecule sequence analysis system of claim 1, wherein the one or more programs are configured to enhance the sequence information.

7. The biomolecule sequence analysis system of claim 1, comprising:

a transportable microdevice comprising wells and an integrated readable memory structure; and a processing station configured to carry out DNA sequencing and comprising an integrated computing portion, a thermal control module, a light source, and a reader unit, the reader unit being configured to read data from the integrated readable memory structure while the transportable microdevice is operably mounted in the processing station.

8. The DNA sequencing system of claim 7, wherein the transportable micro device is a single use disposable unit.

9. The DNA sequencing system of claim 7, further comprising a display for outputting information to a user, wherein the processing station is enclosed in a box, and the box has an exterior, and the display is mounted on the exterior of the box.

10. The DNA sequencing system of claim 9, further comprising a keypad mounted on the exterior of the box and configured to write information to the memory.

11. The DNA sequencing system of claim 7, wherein the reader unit is adapted for communication with the integrated readable memory structure.

12. The DNA sequencing system of claim 7, wherein the integrated computing portion comprising programs installed thereon configured to enhance the sequence information.

* * * * *